(12) United States Patent
Stihl et al.

(10) Patent No.: US 6,261,294 B1
(45) Date of Patent: Jul. 17, 2001

(54) MEDICAL SLIDING-SHAFT INSTRUMENT

(75) Inventors: Ewald Stihl, Geisingen; Andreas Efinger, Rietheim, both of (DE)

(73) Assignee: Karl Storz GmbH & Co. KG (DE)

( * ) Notice: Subject to any disclaimer, the term of this patent is extended or adjusted under 35 U.S.C. 154(b) by 0 days.

(21) Appl. No.: 09/401,200

(22) Filed: Sep. 22, 1999

Related U.S. Application Data

(63) Continuation of application No. PCT/EP99/00398, filed on Jan. 22, 1999.

(30) Foreign Application Priority Data

Jan. 22, 1998 (DE) .............................................. 198 02 145

(51) Int. Cl.⁷ .................................................... A61B 17/32
(52) U.S. Cl. ............................................. 606/83; 606/170
(58) Field of Search .............................. 606/83, 79, 170, 606/184

(56) References Cited

U.S. PATENT DOCUMENTS

| | | | |
|---|---|---|---|
| 4,777,948 | * 10/1988 | Wright | 128/312 |
| 5,273,519 | 12/1993 | Koros et al. | 606/83 |
| 5,385,570 | * 1/1995 | Chin et al. | 606/170 |
| 5,569,258 | * 10/1996 | Gambale | 606/83 |
| 5,653,713 | 8/1997 | Michelson | 606/83 |

FOREIGN PATENT DOCUMENTS

| | | |
|---|---|---|
| 17 12 028 U1 | 12/1955 | (DE) . |
| 41 15 937 A1 | 5/1992 | (DE) . |
| 94 21 125 | 6/1995 | (DE) . |
| 0 706 780 A2 | 4/1996 | (EP) . |

* cited by examiner

Primary Examiner—Gene Mancene
Assistant Examiner—Melba Bumgarner
(74) Attorney, Agent, or Firm—St. Onge Steward Johnston & Reens LLC

(57) ABSTRACT

A sliding-shaft medical instrument has a sliding shaft that has first and second slide elements, arranged side by side and displaceable axially relative to one another, and at least one jaw part at the distal end that is actuable, by way of a handle at the proximal end, via a relative displacement of said two slide elements, said handle having two handle elements that are movable relative to one another. Said first slide element is mounted, in swing-aside fashion, at a distal end of a tubular shaft that is detachably attached to said handle. In order to actuate said at least one jaw part, said tubular shaft is displaceable relative to said second slide element, and said first slide element can be swung aside when said tubular shaft is detached from said handle and is displaced a further distance.

17 Claims, 4 Drawing Sheets

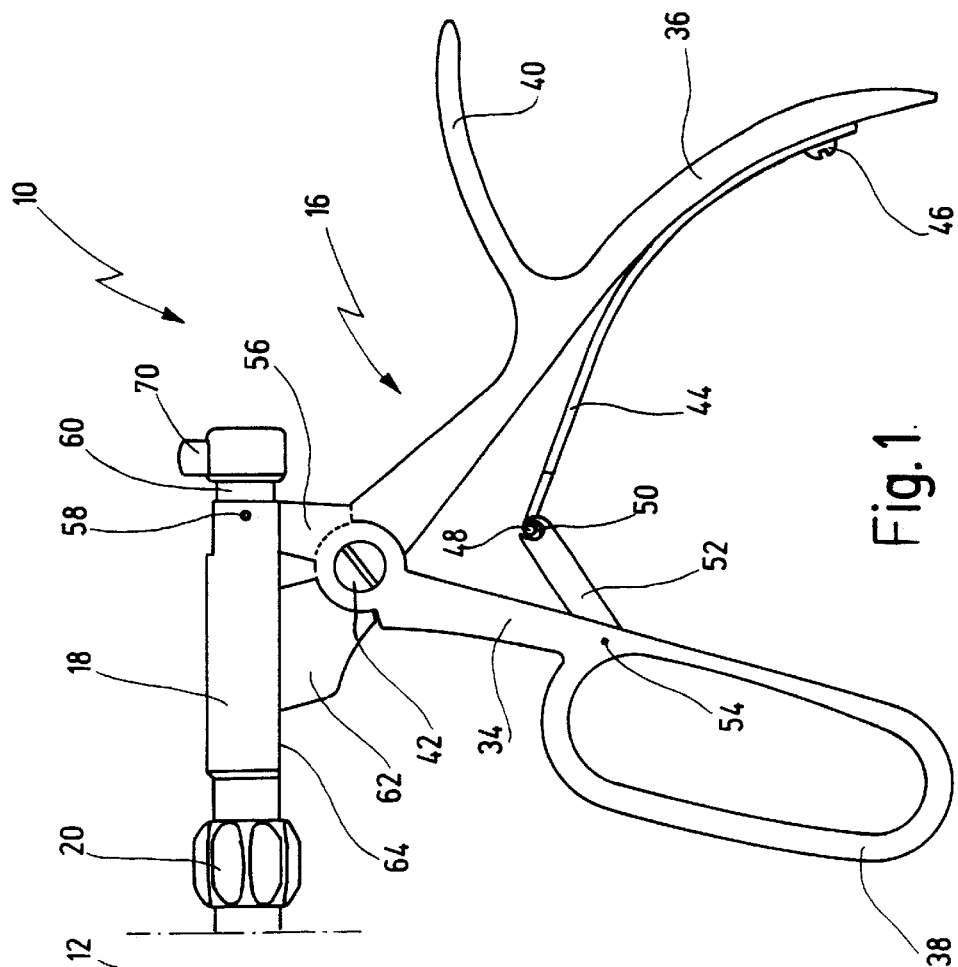
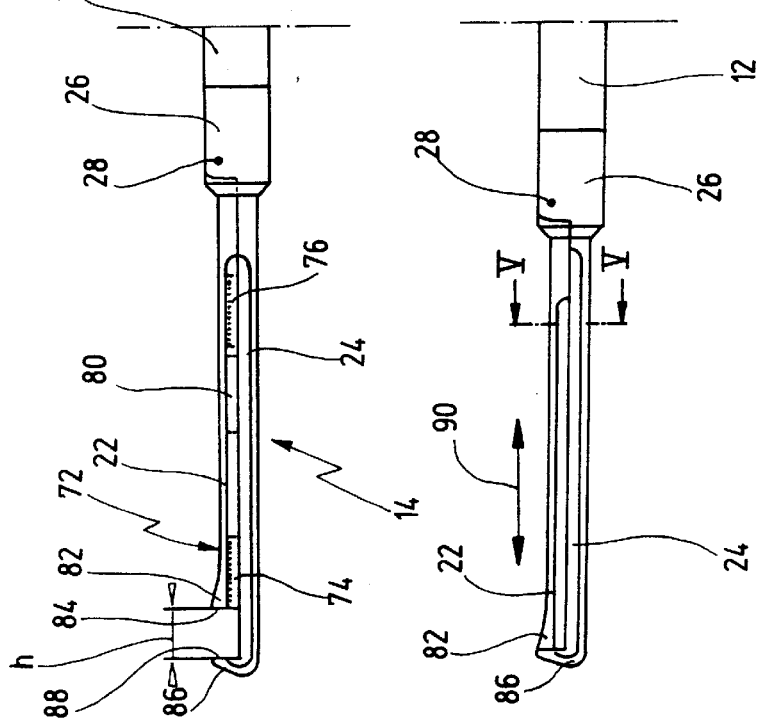

MEDICAL SLIDING-SHAFT INSTRUMENT

CROSS REFERENCE TO PENDING APPLICATION

This application is a continuation of pending International Application PCT/EP99/00398, filed Jan. 22, 1999.

BACKGROUND OF THE INVENTION

The invention relates to a sliding-shaft medical instrument having a sliding shaft that has first and second slide elements, arranged side by side and displaceable relative to one another, having at least one jaw part at a distal end of the sliding shaft, that is actuable, by way of a handle at a proximal end, via a relative displacement of the first and second slide elements, the handle having two handle elements that are movable relative to one another.

A sliding-shaft instrument of this kind is known from DE-A-41 15 937.

A further sliding-shaft instrument of this kind is known from the company brochure of Karl Storz GmbH & Co., Tuttlingen, Germany, entitled "Karl Storz-Endoskope" [Karl Storz endoscopes], section entitled "Instrumente fÿr Nase und Nasenplastik" [Instruments for the nose and rhinoplasty], page N 10 A.

Sliding-shaft instruments are used in endoscopic surgery for surgical operations of various kinds in the human or animal body, sliding-shaft instruments being particularly suitable for transferring large forces even in confined spaces, for example between vertebrae.

The sliding-shaft instrument known from the aforesaid company brochure has a sliding shaft that has two slide elements, arranged side by side and displaceable relative to one another. The one, immovable sliding element is joined immovably to the immovable handle element, while the other slide element is joined displaceably and directly to the movable handle element of the handle at the proximal end. Actuation of the handle causes the movable slide element to be displaced relative to the immovable slide element, so that a jaw part at the distal end of the sliding-shaft instrument can be actuated, for example to detach or grasp tissue.

A disadvantage of the known sliding-shaft instrument, however, consists in the fact that it can be disassembled into its components only inadequately, or at least only with great time expenditure, so cleaning of the sliding-shaft instrument presents difficulties. In particular, contaminants collect between the two slide elements, i.e. more precisely between the mutually contacting sliding surfaces of the two slide elements. In the known sliding-shaft instrument, the region between the slide elements is not accessible, so that it is impossible to guarantee that contaminants between the slide elements can be reliably eliminated.

In the case of longer instruments, however, especially for endoscopically assisted abdominal cavity surgery, it is absolutely necessary that the sliding-shaft instrument be easy to clean.

The sliding-shaft instrument known from the aforesaid DE-A-41 15 937 has a sliding shaft that is also directly joined to the handle. The sliding shaft is configured so that the two slide elements forming the sliding shaft can be separated from one another for easier cleaning once the sliding shaft has been taken off the handle, but this known sliding-shaft instrument is disadvantageous for the following reasons:

In endoscopically assisted operations, the necessary instruments are often inserted through a trocar which presents an opening having a circular cross section. Since a positive pressure is generated in order to make the surgical field accessible, any such instrument in the trocar must seal as tightly as possible and also be securely guided by the trocar.

The aforesaid known sliding-shaft instrument does not guarantee such sealing closure in a trocar, since the sliding shaft extends as far as the handle, and thus upon insertion into a trocar, a positive pressure that has been established in the surgical field can escape outward between the two slide elements that are arranged side by side. A further disadvantage when the known instrument is used with a trocar consists in the fact that one of the two slide elements is in frictional contact with the trocar when the instrument is actuated therein.

Also known, from DE Utility Model 94 21 125, is a surgical forceps that is not a sliding-shaft instrument as defined by the present invention, but rather a tubular-shaft instrument whose tubular shaft has a longitudinal slot in which is guided an actuation rod that is axially movable in the longitudinal slot and is joined at the distal end to a jaw part in order to move it. This tubular-shaft instrument also does not guarantee sealed closure in a trocar, since in this case a positive pressure can escape through the longitudinal slot in the tubular shaft.

A conventional tubular-shaft instrument having a closed tubular shaft is known from DE Utility Model 17 12 028, but it is not a sliding-shaft instrument.

It is therefore the object of the invention to develop a sliding-shaft instrument of the kind cited initially in such a way that it can easily be cleaned and made sterile, and so as to ensure that contaminants on the components, in particular between the slide elements, can be eliminated. An instrument of this kind is moreover intended to ensure the sealing tightness of a trocar through which it is introduced, and to be securely guided and held by the trocar.

SUMMARY OF THE INVENTION

This object is achieved, in terms of the sliding-shaft instrument cited initially, in that the sliding shaft is arranged at the distal end of an elongated tubular shaft that is attached detachably to the handle; that the first slide element is mounted at the distal end of the tubular shaft in swing-aside fashion, that in order to actuate the at least one jaw part, the tubular shaft is displaceable, together with the first slide element, relative to the second slide element, and that the first slide element can be swung aside when the tubular shaft is detached from the handle and is displaced a further distance with respect to the second slide element.

The configuration of the sliding-shaft instrument according to the present invention allows easy and rapid disassembly of the sliding-shaft instrument, and moreover guarantees the requisite sealing tightness and guidance when working through a trocar. Because a tubular shaft is provided between the slide elements and the handle, the instrument fits in secure and sealed fashion into a (usually cylindrical) trocar. Because the first slide element of the sliding shaft is mounted at the distal end of the tubular shaft in swing-aside fashion, the first slide element can be folded out with respect to the second slide element for cleaning of the sliding-shaft instrument, so that the region between the two slide elements is easily accessible for cleaning. Cleaning of the slide elements thus requires simply folding them out away from one another. Since this first slide element is mounted at the distal end of the tubular shaft in swing-aside fashion, provision is furthermore made, according to the present invention, for the tubular shaft to be displaced by way of the handle in order to actuate the at least one jaw part, thus bringing about the relative displacement of the two slide elements, since the first slide element is joined to the tubular shaft. The configuration of the tubular shaft displaceably, according to the present invention, has the advantage that the sliding-shaft instrument can be equipped with a handle such as the one known as the "Take Apart" handle of Karl Storz GmbH, Tuttlingen, Germany, which has proven very successful for medical forceps. Another provision according to the present invention is for the tubular shaft to be detachable from the handle, thus allowing further disassembly of the sliding-shaft instrument. Because the first sliding element can be swung aside only when the tubular shaft is detached from the handle, the result is that the two sliding elements do not fold out away from one another when the sliding-shaft instrument is being used for surgery. Altogether, the invention makes available a sliding-shaft instrument which can be easily and quickly disassembled to the point that the individual components of the sliding-shaft instruments can easily be cleaned, and that all components are accessible for cleaning to such an extent that contaminants can reliably be removed.

The object of the invention is thereby completely achieved.

In a preferred embodiment, the first handle element is movable and the tubular shaft is joined to that handle element.

In this embodiment, the displaceable tubular shaft is therefore joined to the movable handle element, thus achieving the advantage that a movement of the movable handle element is converted directly into movement of the tubular shaft, and interposition of further mechanical actuation elements is avoided.

In a further preferred embodiment, the second slide element is immovable and is joined via a rod element to the second, immovable handle element.

The advantage of this feature is that the rod element can be arranged in the tubular shaft, so that the tubular shaft surrounds the rod element in the manner of a housing and no openings, or very few openings, are formed through which contaminants can penetrate into the sliding-shaft instrument.

In a further preferred embodiment, for actuation of the jaw part the two slide elements are guided relative to one another by way of a guide, the guide being detached upon displacement of the tubular shaft over the further distance.

This feature results in an advantageously simple mechanical configuration of the sliding-shaft instrument according to the invention, in which on the one hand the effect of the guide is that for actuation of the at least one jaw part in a surgical operation, the two slide elements can be displaced slightly with respect to one another without detaching from one another. On the other hand, a guide offers a mechanically simple connection which allows the first slide element to swing aside, when the tubular shaft is displaced by the further distance, by the fact that the guide is then detached.

It is further preferred in this context if the guide has at least one T-shaped groove and one projection with a cross section complementary thereto, and if the groove has at least one enlarged portion that is wider than the width of the projection.

The advantage of this feature is that the T-shaped configuration of the groove and the projection ensures a non-detachable join between the two slide elements during surgical use. The enlarged portion allows the first slide element to swing aside when the projection is displaced relative to the groove to the point that it comes to rest in the enlarged portion of the groove.

In a further preferred embodiment, the first slide element has at its proximal end a sleeve that is detachably attached to the tubular shaft.

The advantage of this feature is that the sliding-shaft instrument according to the present invention is made easier to disassemble, since now the tubular shaft can also be easily detached from the sliding shaft.

It is preferred in this context if the first slide element is joined to the sleeve via a pivot joint.

This feature advantageously brings about pivotable attachment of the first slide element to the tubular shaft.

In a further preferred embodiment, the sleeve is arranged around the second slide element and, in the state detached from the tubular shaft, is displaceable on the second slide element.

The advantage of this feature is that even contaminants that collect between the inner side of the sleeve and the outer side of the second slide element can easily be removed, by displacing the sleeve on the second slide element. This feature further improves the cleanability of the sliding-shaft instrument according to the present invention.

In a further preferred embodiment, the sleeve is attached to the tubular shaft by way of a bayonet-like connector.

The advantage of this feature is that the sleeve can be snap-locked to the tubular shaft by turning it and can just as easily be detached therefrom once again, thus achieving rapid separation of the tubular shaft from the sliding shaft.

In a further preferred embodiment, the first slide element carries at its distal end a first jaw part, and a second jaw part is attached at the distal end of the second slide element, the jaw parts coacting in the manner of a punch when closing.

With this embodiment the sliding-shaft instrument can be used, for example, as a bone punch or tissue punch that has the advantage, not hitherto achieved in conventional bone punches and tissue punches, of being easily disassembled and cleaned.

In an alternative embodiment, the first slide element is joined at its distal end to a first jaw part that is pivotably articulated on a second jaw part that is joined to the second slide element, displacement of the slide elements relative to one another causing the two jaw parts to coact in the manner of a forceps.

With this embodiment according to the present invention, the sliding-shaft instrument can be used as a grasping or cutting forceps, a grasping or cutting forceps of this kind once again having the advantage, as compared to conventional grasping or cutting forceps, of being easier to disassemble and clean.

It is preferred in this context if the first jaw part is detachably joined to the first slide element.

This feature results in the advantage that the first slide element can be swung aside with no need for the two jaw parts, joined to one another in articulated fashion, to be detached from one another. This feature furthermore has the advantage that the jaw parts can also be brought into an easily cleanable position.

In a further preferred embodiment, the first jaw part is automatically detached from the first slide element as the latter pivots aside.

This feature yields the advantage that disassembly of the sliding-shaft instrument according to the present invention can be performed quickly and easily with no need, for that purpose, for manipulations that require particular dexterity.

An automatically detaching connection of this kind between the first jaw part and the first slide element can be achieved, for example, by the fact that an axle pin is present on the first slide element and a recess is present on the first jaw part, the axle pin being lifted out of the recess when the first slide element is pivoted aside.

In a further preferred embodiment, complete detachment of the first jaw part from the second jaw part and/or the first slide element from the sleeve and/or the sleeve from the second slide element is possible.

This feature yields the advantage that all the surfaces of the elements of the distal end can be exposed for cleaning and sterilizing.

Further advantages are evident from the description below of the appended drawings.

It is understood that the features mentioned above and those yet to be explained below can be used not only in the respective combinations indicated, but also in other combinations or in isolation, without leaving the context of the present invention.

BRIEF DESCRIPTION OF THE DRAWINGS

Exemplifying embodiments of the invention are shown in the drawings and will be explained in more detail below. In the drawings:

FIG. 1 shows a sliding-shaft instrument according to a first exemplifying embodiment, in a first operating position;

FIG. 2 shows the distal end of the sliding-shaft instrument of FIG. 1 in a second operating position;

DETAILED DESCRIPTION OF A PREFERRED EMBODIMENT

Figure 3:
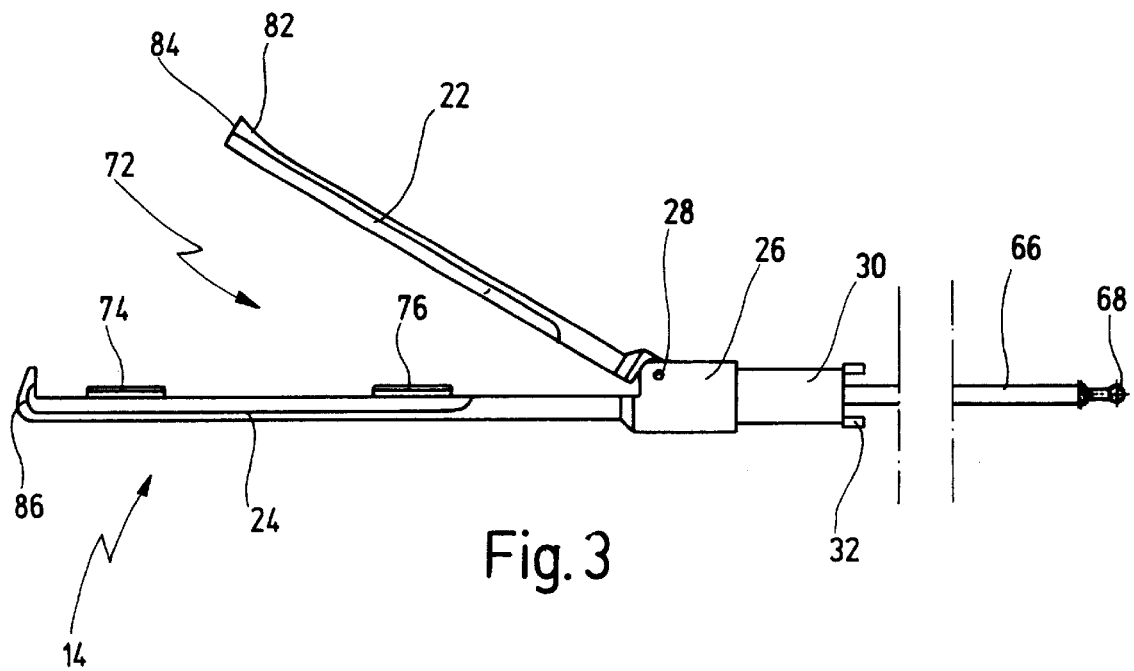
FIG. 3 shows the distal end of the sliding-shaft instrument in FIG. 1 in the cleaning position.

FIG. 1 shows a sliding-shaft instrument labeled in its entirety with the reference numeral 10. Sliding-shaft instrument 10 is used for endoscopic surgical operations in the human or animal body.

Sliding-shaft instrument 10 has a tubular shaft 12 (shown in FIG. 1 with an interruption), a sliding shaft 14 at the distal end, and a handle 16 at the proximal end. Tubular shaft 12, shown in interrupted fashion, is altogether approximately three to four times the length of sliding shaft 14.

Figure 4:
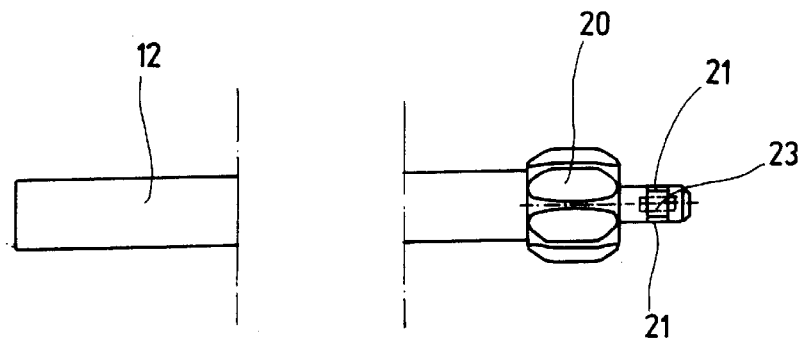
FIG. 4 shows the tubular shaft of the sliding-shaft instrument in FIG. 1 in the state detached from the handle of the sliding-shaft instrument.

Tubular shaft 12 is detachably joined to a tubular portion 18 of handle 16. For that purpose, tubular shaft 12 has a coupling nut 20 that, as shown in FIG. 4, is arranged in lossproof fashion at the proximal end of tubular shaft 12. Coupling nut 20 is thread-joined to threads (not shown) provided on tubular portion 18 (FIG. 1).

Sliding shaft 14 has a first slide element 22 and a second slide element 24 that are arranged side by side.

First slide element 22 is mounted on tubular shaft 12, at its distal end, in swing-aside fashion; FIG. 3 show first slide element 22 in the swung-aside position, without tubular shaft 12. First slide element 22 is attached to a sleeve 26 via a pivot joint 28. Sleeve 26 is in turn arranged around second slide element 24 and is displaceable relative thereto. Sleeve 26 furthermore has at its proximal end a sleeve extension 30 that carries projections 32 at its proximal end. In FIG. 1, sleeve extension 30 is inserted into the distal end of tubular shaft 12; recesses (not shown) into which projections 32 can be introduced are present in the inner wall of the distal end of tubular shaft 12, and sleeve 26 is snap-locked to tubular shaft 12 by approximately a quarter-turn relative to tubular shaft 12. Projections 32 and the corresponding recesses thus form a bayonet-like connector for sleeve 26 on tubular shaft 12.

Handle 16 furthermore has a first handle element 34 and a second handle element 36. First handle element 34 is movable, while second handle element 36 is immovable.

First handle element 34 has a ring 38 through which one or more of the operator's fingers can be passed. Immovable handle element 36 has a bracing element 40 protruding proximally therefrom. When sliding-shaft instrument 10 is being used in a surgical operation, immovable handle element 36 lies between the thumb and index finger of the operator's hand, while bracing element 40 prevents the hand from slipping. Movable handle element 34 is joined to immovable handle element 36 via a pivot joint 42. Pivot joint 42 is constituted by corresponding bores in movable handle element 34 and by a bolt, passed through immovable handle element 36, that is fastened at the opposite end using a nut or the like.

In addition, there is arranged between movable handle element 34 and immovable handle element 36 a leaf spring 44 that is attached by way of a screw 46 to immovable handle element 36. Arranged at the distal end of leaf spring 44 is a peg 48 that is inserted into a recess 50 of a spring holder 52. Spring holder 52 is in turn attached to movable handle element 34 via a pivot joint 54. The result of leaf spring 44 is that movable handle element 34 and immovable handle element 36 are preloaded into their idle position shown in FIG. 1, i.e. that leaf spring 44 pushes handle elements 34 and 36 apart.

One end 56 of movable handle element 34 is joined to tubular portion 18 via a pivot joint 58 that also allows a slight lateral movement. Tubular portion 18 sits, axially displaceably in the manner of a carriage, on a immovable element 60 of handle 16, to which one end 62 of immovable handle element 36 is attached by the fact that end 62 engages through a longitudinally extending slot 64 configured on the underside of tubular portion 18.

Second slide element 24 is immovably joined to a rod element 66 (see FIG. 3) that has at its proximal end a ball 68 that is in engagement with a corresponding recess (not shown) in immovable element 60. Provided for that purpose at the proximal end of immovable element 60 is a pushbutton 70; when this is actuated by being pushed down, ball 68 can be introduced into the corresponding recess in immovable element 60, and is locked when pushbutton 70 is released.

Rod element 66 is of a length such that it projects beyond tubular shaft 12 at the proximal end. Rod element 66 extends in tubular shaft 12 and a portion of immovable element 60, and is therefore not visible in FIG. 1. Rod element 66 has in the proximal region a flattened area into which engage two movable half-shells 21, mounted on tubular shaft 12, that are held together by an elastic ring 23. When tubular portion 18 is placed onto tubular shaft 12, half-shells 21 are pressed against the flattened area so that rotation and thus unlocking of sleeve 26 are impossible. This ensures that disassembly of the instrument must begin with removal of handle 16.

Altogether, second slide element 24 is immovably joined, via rod element 66 that passes through tubular shaft 12 as far as the recess in immovable element 60, to immovable element 60 and thus to immovable handle element 36. First slide element 22, on the other hand, is joined via sleeve 26, tubular shaft 12, and tubular portion 18 to movable handle element 34, and can be displaced relative to second slide element 24 by displacing tubular shaft 12.

Figure 5:
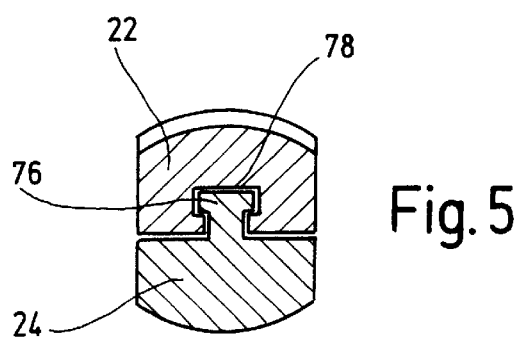
FIG. 5 shows a cross section, along line V—V in FIG. 2, through the sliding shaft of the sliding-shaft instrument in FIG. 1.
Figure 6:
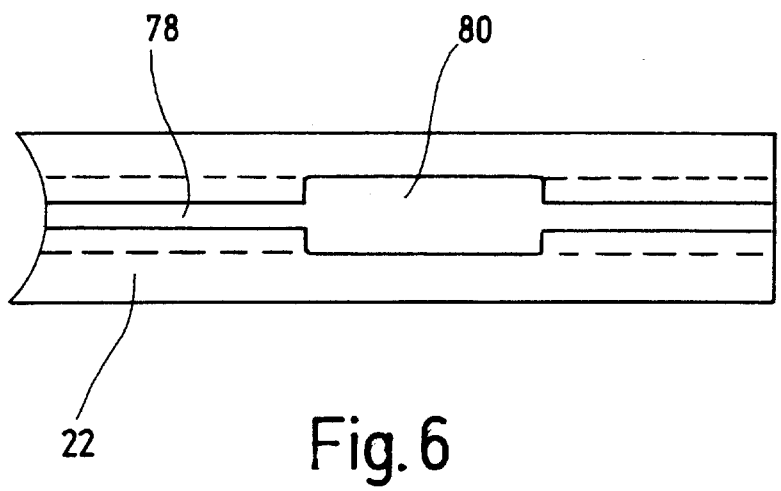
FIG. 6 shows a view from below of the first slide element of the sliding shaft of the sliding-shaft instrument in FIG. 1.

When sliding-shaft instrument 10 is in the utilization state, first slide element 22 and second slide element 24 are joined to one another via a guide 72. For this purpose, second slide element 24 has two longitudinally extending projections 74 and 76, spaced axially apart from one another, that engage into a groove 78 configured in first slide element 22. Projections 74 and 76 have a T-shaped cross section, groove 78 having a cross section that is also T-shaped and complementary thereto (see FIG. 5). Groove 78 has an enlarged portion 80 which defines an opening that is wider than the overall width of projection 76. Projection 76 can thus be inserted through enlarged portion 80 into groove 78, as will be explained later. Groove 78 is moreover open at the distal end of first slide element 22.

In addition, first slide element 22 has at its distal end a first jaw part 82 at whose distal end a cutting edge 84 is configured. Second slide element 24 has a second jaw part 86 that has a cutting edge 88 at its proximal end.

The manner of operation of sliding-shaft instrument 10 will now be described below.

In FIG. 1, sliding-shaft instrument 10 is shown in a first operating position, i.e. the idle position. In this state, first slide element 22 and second slide element 24 rest alongside one another, projections 74 and 76 engaging into groove 78. Also in FIG. 1, h indicates the maximum opening position of jaw parts 82 and 86 in surgical use, corresponding at the same time to the working stroke of sliding shaft 14, i.e. more precisely of first slide element 22.

When movable handle element 34 is then moved toward immovable handle element 36, end 56 of movable handle element 34, which engages on movable tubular portion 18, displaces tubular shaft 12 toward the distal end. Because of the displacement of tubular shaft 12, first slide element 22 (which is joined via sleeve 26 to tubular shaft 12) is also displaced toward the distal end, causing jaw part 82 to be displaced toward jaw part 86. Cutting edges 84 and 88 coact in the manner of a punch as jaw parts 82 and 86 are closed, so that sliding-shaft instrument 10 can be used to punch bone or tissue. A very large force can be applied in this context, since the relatively thin rod element 66 is stressed only in tension. In FIG. 2, the distal end of sliding-shaft instrument 10 is shown in an operating position in which jaw parts 82 and 86 are completely closed, and tubular shaft 12 is maximally displaced toward the distal end relative to second slide element 24.

When the manual force exerted on movable handle element 34 is reduced again, leaf spring 44 causes movable handle part 34 to be moved back into its original position, causing tubular shaft 12 to be displaced or pulled back toward the proximal end of sliding-shaft instrument 10. Jaw parts 82 and 86 thereby open again.

The movement of movable handle element 34 toward and away from immovable handle element 36 thus causes first sliding element 22 to be displaced, as shown by a double arrow 90, relative to second slide element 24 in order to actuate jaw parts 82 and 86. During this displacement, projections 74 and 76 of second slide element 24 are in engagement with groove 78 of first slide element 22 over the entire working stroke h, in such a way that projections 74 and 76 do not enter into enlarged portion 80 of groove 78 or emerge from the distal end of groove 78, so that first slide element 22 cannot swing aside unintentionally.

The manner in which sliding-shaft instrument 10 can be disassembled will now be described below.

First, coupling nut 20 is threaded completely off. Push-button 70 is then pushed down, which allows ball 68 at the proximal end of rod element 66 to be pulled off immovable element 60. The assembly consisting of sliding shaft 14, tubular shaft 12, and rod element 66 can then be pulled off together from handle 16. Half-shells 21 on tubular shaft 12 are then exposed.

Displacing tubular shaft 12 relative to second slide element 24 a further distance toward the proximal end, that distance being specifically the length of projection 74 or projection 76, now causes projection 74 to come out of groove 78 out of its distal-end opening, while projection 76 comes to rest in enlarged portion 80 of groove 78. First slide element 22 can now be folded away from second slide element 24 by way of pivot joint 28 on sleeve 26. It is thus particularly easy to clean sliding shaft 14 in the region between first slide element 22 and second slide element 24.

Sliding shaft 14 can be removed further from tubular shaft 12 by rotating sleeve 26 a quarter-turn with respect to tubular shaft 12, thus undoing the bayonet-like connector constituted by projections 32. In FIG. 3, tubular shaft 12 has already been removed from sliding shaft 14, while rod element 66 remains immovably joined to second slide element 24. Sleeve 26 can now be axially displaced on second slide element 24, so that the inner side of sleeve 26, and the region of second slide element 24 on which sleeve 26 is axially displaceable during use, can easily be cleaned. All the poorly accessible regions of sliding-shaft instrument 10 can thus be disassembled or exposed in such a way as to guarantee that contaminants can be reliably removed even from these regions and sliding-shaft instrument 10 can be made sterile.

Figure 7:
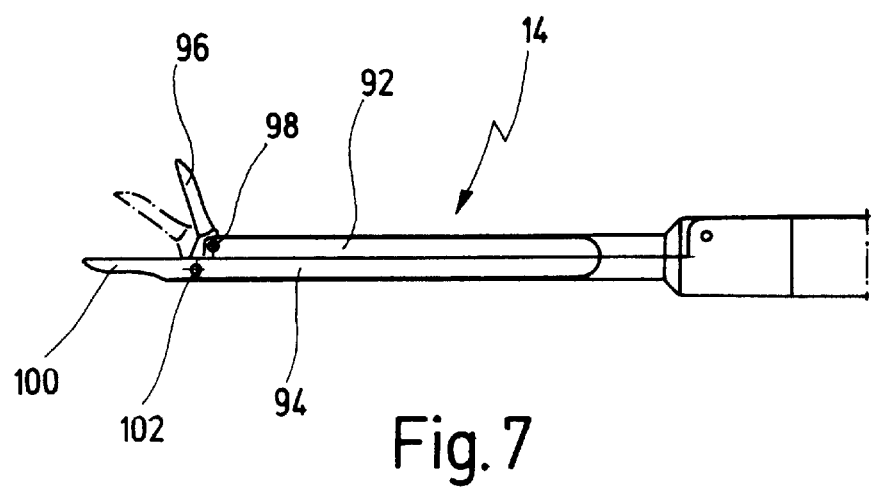
FIG. 7 shows the distal end of a sliding-shaft instrument according to the present invention in accordance with a second exemplifying embodiment, in a first operating position.
Figure 8:
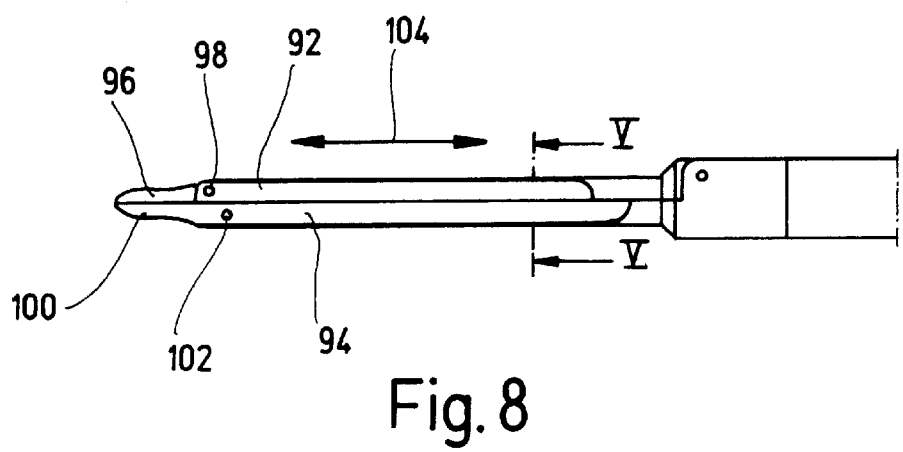
FIG. 8 shows the distal end of the sliding-shaft instrument in FIG. 7 in a second operating position.
Figure 9:
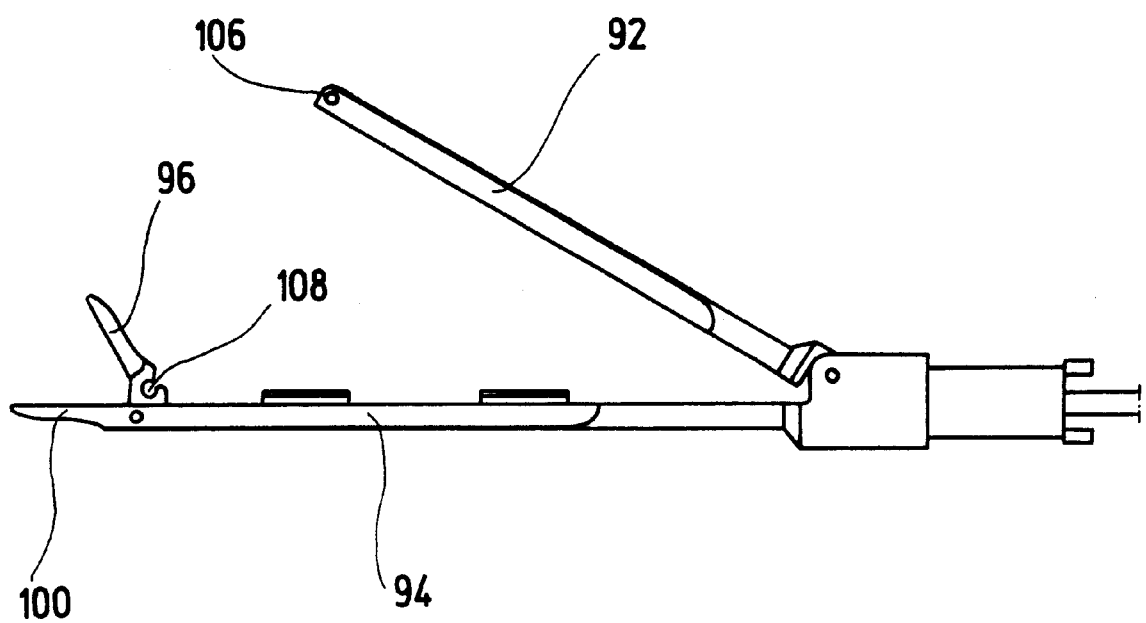
FIG. 9 shows the distal end of the sliding-shaft instrument in FIGS. 7 and 8 in the cleaning position.

FIGS. 7 through 9 depict a further exemplifying embodiment that differs from the exemplifying embodiment shown in FIGS. 1 through 6 only in terms of the jaw parts at the distal end of sliding shaft 14. With this kind of configuration of the jaw parts, sliding-shaft instrument 10 can be used as a cutting or grasping forceps.

For example, there is arranged at the distal end of a first slide element 92, which in turn is displaceable with respect to a second slide element 94, a first jaw part 96 that is joined via a pivot joint 98 to first sliding element 92. In addition, first jaw part 96 is articulated on a second jaw part 100 via a pivot joint 102.

A displacement of first slide element 92 relative to second slide element 94, as shown by a double arrow 104, causes first jaw part 96 to close against second jaw part 100 as shown in FIG. 8, or to open as shown in FIG. 7. The closing movement of first jaw part 96 is achieved by the fact that axial displacement of first slide element 92 causes pivot joint 98 to be displaced toward the distal end with respect to pivot joint 102, thus pivoting first jaw part 96 about pivot joint 102. In this embodiment as well, the closing movement can be accomplished with a great deal of force, since the relatively thin rod element 66 once again is stressed only in tension.

Displacement of first slide element 92 over a further distance—which is possible, as in the case of the first exemplifying embodiment, only after handle 16 has been detached—causes the connection between first slide element 92 and first jaw part 96 in the region of pivot joint 98 to be undone. For this purpose, pivot joint 98 is configured by attaching to first slide element 92 an axle pin 106 that engages into a recess 108 on first jaw part 96 and, upon displacement over a further distance, automatically comes out of recess 108.

First slide element 92 is once again, as in the case of the first exemplifying embodiment, configured in swing-aside fashion. When first slide element 92 is swung aside, the tubular shaft is displaced even farther toward the proximal end with respect to second slide element 94, the guide being detached.

What is claimed is:

1. A medical sliding-shaft instrument, comprising
    a sliding shaft having first and second slide elements arranged side by side and displaceable axially relative to one another,
    at least one jaw part disposed at a distal end of said sliding shaft,
    a handle disposed at a proximal end of said instrument and having first and second handle elements movable relative to one another,
    said at least one jaw part being actuable by way of said handle via a relative distance of displacement of said first and second slide elements,
    wherein
        said instrument further comprises an elongated tubular shaft detachably attached to said handle,
        said sliding shaft is arranged at a distal end of said elongated tubular shaft,
        said first slide element of said sliding shaft is mounted at said distal end of said tubular shaft in swing-aside fashion,
        said tubular shaft is displaceable, together with said first slide element, relative to said second slide element in order to actuate said at least one jaw part, and
        said first slide element can be swung aside when said tubular shaft is detached from said handle and said tubular shaft is displaced a further distance with respect to said second slide element.

2. The sliding-shaft instrument of claim 1, wherein said first handle element is movable and said tubular shaft is joined to said first handle element.

3. The sliding-shaft instrument of claim 1, wherein said second slide element is immovable and is joined via a rod element to said second, immovable handle element.

4. The sliding-shaft instrument of claim 1, wherein for actuation of said at least one jaw part, said first and second slide elements are guided relative to one another by way of a guide, said guide being detached upon displacement of said tubular shaft over said further distance.

5. The sliding-shaft instrument of claim 4, wherein said guide has at least one groove and at least one projection, said groove having a T-shaped cross section and said projection a cross section complementary thereto, said groove having an enlarged portion that is wider than the width of said projection.

6. The sliding-shaft instrument of claim 1, wherein said first slide element has at its proximal end a sleeve that is detachably attached to said tubular shaft.

7. The sliding-shaft instrument of claim 6, wherein said first slide element is completely detachable from said sleeve.

8. The sliding-shaft instrument of claim 7, wherein said first slide element is joined to said sleeve via a pivot joint.

9. The sliding-shaft instrument of claim 1, wherein said first slide element has at its proximal end a sleeve that is detachably attached to said tubular shaft, and said first slide element is joined to said sleeve via a pivot joint.

10. The sliding-shaft instrument of claim 1, wherein said first slide element has at its proximal end a sleeve that is detachably attached to said tubular shaft, and wherein said sleeve slidably receives said second slide element, and, when said sleeve is detached from the tubular shaft said sleeve, is displaceable on said second slide element.

11. The sliding-shaft instrument of claim 10, wherein said sleeve is completely detachable from said second slide element.

12. The sliding-shaft instrument of claim 1, wherein said first slide element has at its proximal end a sleeve that is detachably attached to said tubular shaft, and wherein said sleeve is attached to said tubular shaft by way of a bayonet-like connector.

13. The sliding-shaft instrument of claim 1, wherein said first slide element carries at its distal end a first jaw part, and a second jaw part is attached at a distal end of said second slide element, said two jaw parts coacting in the manner of a punch when closing.

14. The sliding-shaft instrument of claim 1, wherein said first slide element carries at its distal end a first jaw part, which is pivotably articulated on a second jaw part attached at a distal end of said second slide element, displacement of said first and second slide elements relative to one another causing said two jaw parts to coact in the manner of a forceps.

15. The sliding-shaft instrument of claim 14, wherein said first jaw part is detachably joined to said first slide element.

16. The sliding-shaft instrument of claim 1, wherein said first slide element carries at its distal end a first jaw part, which is pivotably articulated on a second jaw part attached at a distal end of said second slide element, displacement of said first and second slide elements relative to one another causing said two jaw parts to coact in the manner of a forceps, and wherein said first jaw part is completely detachable from said first slide element.

17. The sliding-shaft instrument of claim 1, wherein said first slide element carries at its distal end a first jaw part, which is pivotably articulated on a second jaw part attached at a distal end of said second slide element, displacement of said first and second slide elements relative to one another causing said two jaw parts to coact in the manner of a forceps, and wherein said first jaw part is automatically detached from said first slide element as the first slide element pivots aside.

* * * * *